US 9,009,898 B2

(12) United States Patent
Morimura et al.

(10) Patent No.: US 9,009,898 B2
(45) Date of Patent: Apr. 21, 2015

(54) MATTRESS, PRESSURE SENSOR CALIBRATION METHOD, AND BED DEVICE

(71) Applicant: Paramount Bed Co., Ltd., Tokyo (JP)

(72) Inventors: Hisao Morimura, Tokyo (JP); Makoto Tanaka, Tokyo (JP); Shinsuke Watanabe, Tokyo (JP)

(73) Assignee: Paramount Bed Co., Ltd., Tokyo (JP)

( * ) Notice: Subject to any disclaimer, the term of this patent is extended or adjusted under 35 U.S.C. 154(b) by 0 days.

(21) Appl. No.: 14/359,405

(22) PCT Filed: Nov. 20, 2012

(86) PCT No.: PCT/JP2012/080047
§ 371 (c)(1),
(2) Date: May 20, 2014

(87) PCT Pub. No.: WO2013/077313
PCT Pub. Date: May 30, 2013

(65) Prior Publication Data
US 2015/0000044 A1   Jan. 1, 2015

(30) Foreign Application Priority Data
Nov. 21, 2011   (JP) ................................. 2011-253769

(51) Int. Cl.
*A47C 27/08*   (2006.01)
*A61B 5/00*   (2006.01)
*A61G 7/057*   (2006.01)
*G01L 27/00*   (2006.01)

(52) U.S. Cl.
CPC ............. *A47C 27/083* (2013.01); *A47C 27/084* (2013.01); *A61B 5/447* (2013.01); *A61B 5/6892* (2013.01); *A61B 2560/0223* (2013.01); *A61B 2560/0247* (2013.01); *A61B 2562/046* (2013.01); *A61B 2562/168* (2013.01); *A61G 7/05769* (2013.01); *A61G 7/05776* (2013.01); *A61G 2203/34* (2013.01); *G01L 27/002* (2013.01); *G01L 27/005* (2013.01)

(58) Field of Classification Search
USPC ................... 5/706, 710, 713, 715, 655.3, 657
See application file for complete search history.

(56) References Cited

U.S. PATENT DOCUMENTS

| | | | | |
|---|---|---|---|---|
| 5,848,450 | A * | 12/1998 | Oexman et al. | 5/713 |
| 6,009,580 | A * | 1/2000 | Caminade et al. | 5/713 |
| 6,094,762 | A * | 8/2000 | Viard et al. | 5/713 |
| 7,107,642 | B2 * | 9/2006 | Wong et al. | 5/713 |
| 8,104,126 | B2 * | 1/2012 | Caminade et al. | 5/715 |

FOREIGN PATENT DOCUMENTS

| | | |
|---|---|---|
| JP | 5-049529 A | 3/1993 |
| JP | 2007-159822 A | 6/2007 |

* cited by examiner

*Primary Examiner* — Fredrick Conley
(74) *Attorney, Agent, or Firm* — Birch, Stewart, Kolasch & Birch, LLP

(57) ABSTRACT

When pressure detected by a pressure sensor connected to a calibration standard cell has continuously fallen within a regulated pressure range at calibration for a regulated duration at calibration, zero-adjustment is performed based on the pressure value detected by the pressure sensor. Then, communication between the plurality of cells is created to perform internal pressure adjustment of the plurality of cells to a predetermined internal pressure value, based on the pressure value detected by the pressure sensor connected to the calibration standard cell and calibrate each of pressure sensors connecting to the plurality of cells, based on the adjusted internal pressure. With this scheme, it is possible to a mattress and the like that can perform zero-point adjustment efficiently by adjusting the zero point in the same manner even if the mattress is formed of a plurality of branches, without releasing the pressure sensor of each cell to atmospheric pressure.

9 Claims, 14 Drawing Sheets

FIG. 9

| Branch A | Weight [kg] | | | | | | |
|---|---|---|---|---|---|---|---|
| | 30 | 35 | 40 | 45 | 50 | 55 | ... |
| Back Angle [deg.] 0~30 | 10 | 10 | 11 | 11 | 12 | 12 | ... |
| 3 2 | 11 | 11 | 11 | 12 | 12 | 13 | ... |
| ... | ... | ... | ... | ... | ... | ... | ... |

MATTRESS, PRESSURE SENSOR CALIBRATION METHOD, AND BED DEVICE

TECHNICAL FIELD

The present invention relates to a mattress and the like including a plurality of cells, pressure sensors for directing the internal pressure of cells, a pump connected to regulate the air quantities in individual cells, and communication paths connected from one pump to the plurality of cells.

BACKGROUND ART

The air mattress formed of cells inflated by air pressure has been conventionally known. The air mattress is used as a Body pressure dispersion mattress and the like, and this mattress is useful for presenting bedsores from occurring over the body of a patient by dispersing the load of the body of the patient lying over the mattress to reduce the pressure acting on the body.

Herein, for individual cells of the air mattress, it is necessary to regulate the pressure inside each cell within a prescribed range (which will be referred to hereinbelow as "internal pressure control"). In order to perform internal pressure control, the pressure is measured first using a pressure sensor, then based on the measured pressure, each cell is inflated or deflated to regulate the pressure.

Herein, before performing internal pressure control, zero-point adjustment should be performed in order to measure pressure correctly. As a method for performing zero-point adjustment, a device disclosed in Patent Document 1 has been known, for instance.

PRIOR ART DOCUMENT

Patent Document

Patent Document 1:
Japanese Patent Application Laid-open 2007-159822

SUMMARY OF THE INVENTION

Problems to be Solved by the Invention

Herein, when zero-point adjustment is performed, it is necessary to release the cells to atmospheric pressure, namely 0 kPa. However, it is impossible to release the pressure sensor in the air mattress having a configuration that continuously measures and adjusts the pressure of the cells when the patient is lying in bed, hence perform normal zero-point adjustment.

Further, the air mattress is formed of a plurality of branches of cells, each branch being prodded with a pressure sensor. For these cells, when zero-point adjustment is performed for each branch it is necessary to perform adjustment by switching the branches one to another as in the apparatus described in the aforementioned Patent Document 1, which has been quite inconvenient.

In view of the problem as above, it is therefore an object of the present invention to provide a mattress and the like that can perform zero-point adjustment efficiently by adjusting the zero-point in the same manner even if the mattress is formed of a plurality of branches, without releasing the pressure sensor of each cell to atmospheric pressure.

Means for Solving the Problems

In view of the above object, a mattress of the present invention is one including a plurality of cells; pressure sensors for detecting the internal pressure of the cells; a pump connected to adjust the amount of air in each cell; communication paths from the pump to the plurality of cells; selector valves, arranged on the communication paths between each of the cells and the pump, and capable of switching between, at least, a state for creating communication between the cell and the pump and a state for opening the cell to atmospheric pressure; and a calibration means for calibrating the pressure sensors, and is characterized in that
the calibration means includes:
a calibration determining means that adopts one cell as a calibration standard cell, determines whether a pressure detected by a pressure sensor connected to the calibration standard cell has continuously fallen within a regulated pressure range at calibration for a regulated duration at calibration when a selector valve connected to the calibration standard cell is opened to atmospheric pressure;
a first calibration means that, when the pressure detected by the pressure sensor connected to the calibration standard cell has continuously fallen within the regulated pressure range at calibration for the regulated duration at calibration, performs zero-point adjustment of the pressure sensor connected to the calibration standard cell, based on a pressure value detected by the pressure sensor;
an internal pressure adjustment means that creates communication between the plurality of cells to perform internal pressure adjustment of the plurality of cells to a predetermined internal pressure value, based on the pressure value detected by the pressure sensor connected to the calibration standard cell; and,
a second calibration means that calibrates each of the pressure sensors connected to the plurality of cells, based on the internal pressure adjusted by the internal pressure adjustment means.

The mattress of the present invention is characterized in that the selector valves installed for the plurality of cells are changed over to communicate with the pump so as to make the plurality of cells hare the same pressure.

The mattress of the present invention further comprises an inter-cell selector valve for creating communication between the plurality of cells, and is characterized in that the internal pressure adjustment means opens the inter-cell selector valve to thereby make the plurality of cells have the same pressure.

The mattress of the present invention further comprises a mattress status detecting means for detecting a state of the mattress, and is characterized in that the calibration means performs calibration of the pressure sensors when the mattress is in a state in which calibration of the pressure sensor is calibratable.

A pressure sensor calibration method of the present invention is one that is used for a mattress including a plurality of cells; pressure sensors for detecting internal pressure of the cells; a pump connected to adjust the amount of air in each cell; communication paths from the pump to the plurality of cells; and a selector valve, arranged on the communication paths between each of the cells and the pump, and capable of switching between, at least, a state for creating communication between the cell and the pump and a state for opening the cell to atmospheric pressure, and a calibration step for calibrating the pressure sensors, comprising the steps of:
determining whether a pressure detected by a pressure sensor connected to the calibration standard cell has continuously fallen within a regulated pressure range at calibration for a regulated duration at calibration when a selector valve connected to the calibration standard cell
is opened to atmospheric pressure;

performing zero-point adjustment of the pressure sensor
connected to the calibration standard cell, based on a
pressure value detected by the pressure sensor when the
pressure detected by the pressure sensor connected to
the calibration standard cell has continuously fallen
within the regulated pressure range at calibration for the
regulated duration at calibration;

creating communication between the plurality of cells to
perform internal pressure adjustment of the plurality of
cells to a predetermined internal pressure value, based
on the pressure value detected by the pressure sensor
connected to the calibration standard cell; and, calibrating each of pressure sensors connected to the plurality of cells, based on the internal pressure adjusted by
the internal pressure adjustment means.

A bed device of the present invention is one including: a
mattress including a plurality of cells; pressure sensors for
defecting internal pressure of the cells; a pump connected to
adjust are amount of air in each cell; and communication
paths from the pump to plurality of cells, a bed body;

selector valves, arranged or the communication paths
between each of the cells and the pump, and capable of
switching between, at least, a state for creating communicating between the cell and the pump and a state for
opening the cell to atmospheric pressure; and, a calibration means for calibrating the pressure sensor, and
is characterized in that the calibration means includes:

a calibration determining means that adopts one cell as a
calibration standard cell, determines whether a pressure
detected by a pressure sensor connected to the calibration standard cell has continuously fallen within a regulated pressure range at calibration for a regulated duration at calibration when a selector valve connected to the
calibration standard cell is opened to atmospheric pressure;

a first calibration means that, when the pressure detected by
the pressure sensor connected to the calibration standard
cell has continuously fallen within the regulated pressure range at calibration for the regulated duration at
calibration, performs zero-adjustment of the pressure
sensor connected to the calibration standard cell, based
on a pressure value detected by the pressure sensor;

an internal pressure adjustment, means that creates communication between the plurality of cells to perform
internal pressure adjustment or the plurality of cells to a
predetermined internal pressure value, based on the
pressure value detected by the pressure sensor connected to the calibration standard cell; and, a second calibration means that calibrates each of the pressure sensors connected to the plurality of cells, based on
the internal pressure adjusted by the internal pressure
adjustment means.

The bed device of the present invention further comprises
a bed status detecting means for detecting a state of the bed
body, and is characterized in that the calibration means performs calibration of the pressure sensors when the bed body
is in a state in which calibration of the pressure sensor is
calibratable.

Advantages of the Invention

The process of the present invention determines whether
the pressure detected by the pressure sensor connected to the
calibration standard cell has continuously fallen within a
regulated pressure range an calibration for a regulated duration at calibration when the selector valve connected to the
calibration standard cell is opened to atmospheric pressure,
performs zero-point adjustment of the pressure sensor connected to the calibration standard cell, based on the pressure
value detected by the pressure sensor when the pressure
detected by the pressure sensor connected to the calibration
standard cell has continuously fallen within the regulated
pressure range at calibration for the regulated duration at
calibration, then creates communication of the selector valves
for the plurality of cells to perform internal pressure adjustment of the plurality of cells to a predetermined internal
pressure value, based on the pressure value detected by the
pressure sensor connected to the calibration standard cell. As
a result, it is possible to perform zero-point adjustment based
on the calibration standard cell and implement calibration of
the pressure sensors connected to the other cells using the
calibration result.

That is, since all the pressure sensors can be calibrated by
opening a lower number of cells to atmospheric pressure,
even if a person lies on the mattress if is possible to calibrate
the pressure sensors while presenting concentration of the
body pressure.

BRIEF DESCRIPTION OF DRAWINGS

FIG. 9 A diagram showing one example of the data structure of internal pressure setting tables in the present embodiment.

MODES FOR CARRYING OUT THE INVENTION

Hereinbelow, the modes for carrying out the present invention will be described with reference to the drawings.

1. Overall Structural View

[1.1 Device Overview]

Figure 1:
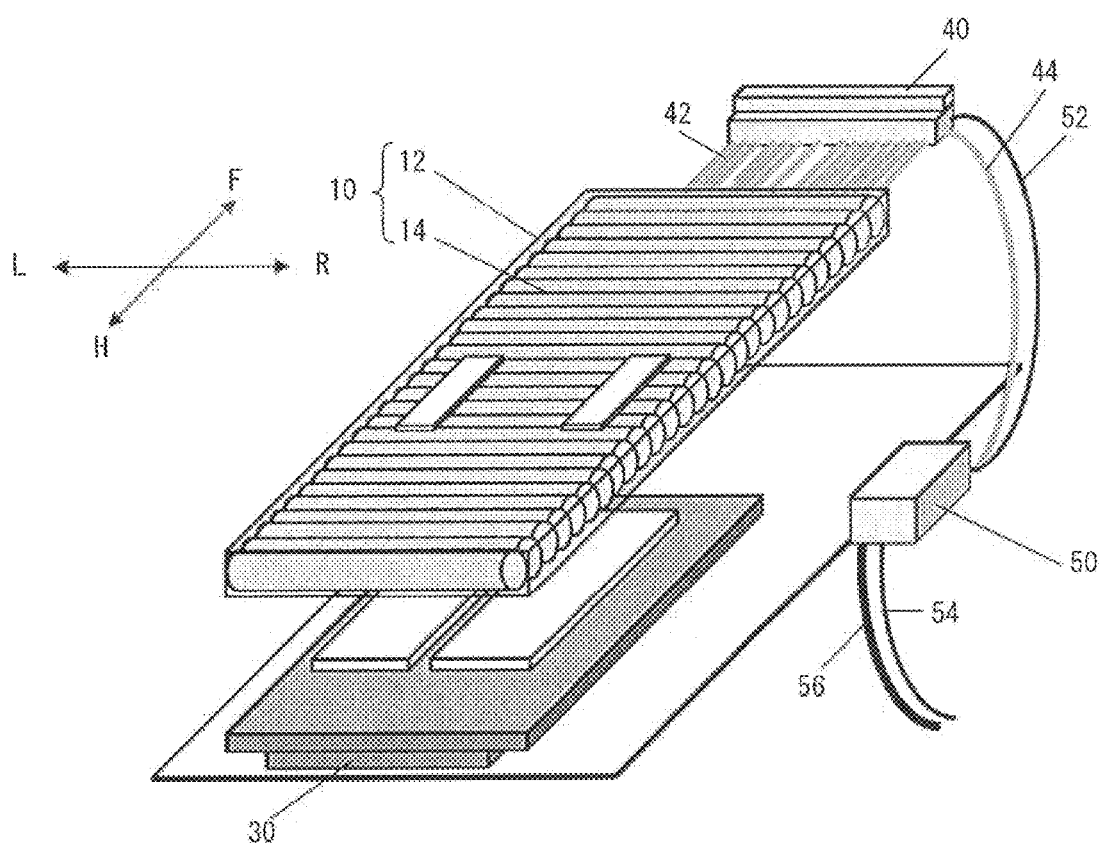
FIG. 1 A diagram for illustrating the overall structure of a
bed device in the present embodiment.
Figure 2:
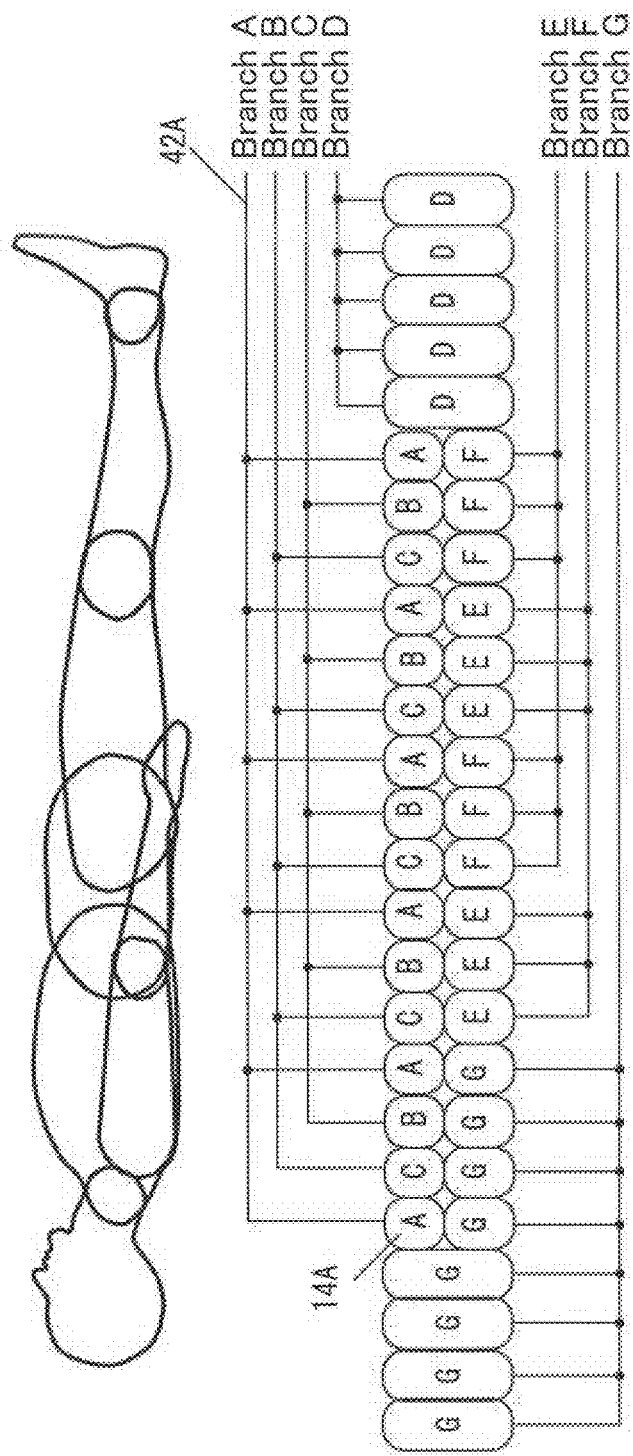
FIG. 2 A diagram for illustrating individual calls of the bed
device in the present embodiment.

To begin with, the overall configuration of a bed device to
which the present invention is applied will be described with reference to FIGS. 1 and 2. FIG. 1 is a diagram for illustrating the overview of a bed device 1 in the present embodiment. FIG. 2 is a front view showing bed device if viewed from the foot side (the controller 40 side in FIG. 1).

Bed device 1 includes a mattress body 10 mounted on a base 30. Herein, mattress body 10 is formed of a plurality of cells 14 arranged contiguously in the longitudinal direction. These cells are enfolded by a cover 12 of a top cover and a bottom cover, to form mattress body 10.

Connected to individual cells (cells 14) are air blow tubes 42 from a controller 40. An air blow tube 41 from a pump unit 50 is connected to controller 40. Further, controller 40 and pump unit 50 are connected to each other by a controllable 52 so that various control signals are exchanged therebetween. Connected to pump unit 50 is a control cable 54 from without as well as a power cable 56 for driving the pump.

Individual cells 14 are separated into plural branch groups, the cells of each branch group being connected to a common air blow tube 12 as a communication path. Air blow tube 42 is connected to a selector valve by way of an air blow tube connector. The selector valve is connected to pump unit 50 by way of the air blow tube. Thus, the operation of pump unit 50 and the selector valve inflates and deflates individual cells.

Here, air blow tubes 42 as the communication paths may be constructed so that a single tube output from pump unit 50 is branched into a plurality of tubes each of which is input to individual branch, or so that a plurality of tubes are output from pump unit 50. In other words, any configuration may be accepted as long as each cell can be made to take the same pressure value with others when an operation for making each cell communicate with others.

[1.2 Explanation of the Individual Cell Configuration]

Next, the configuration of each cell (cell 14) will be described with reference to FIG. 2.

The cells are separated into branches A to G, each connected to pump unit 50. For example, cells 14A are connected to air blow tube 42A as branch A. All cells 14A belonging to branch A are equally inflated or deflated by air blow tube 42A.

[1.3 Operation of Selector Valves]

Next, the operation of selector valves will be described with reference to FIGS. 3 to 7. Here, for description convenience, the operation of the selector valves will be described by giving an example where three cell branches are connected.

In the drawing, cell branch 1 (14a), cell branch 2 (14b) and cell branch 3 (14c) are illustrated. In each cell branch, an air blow tube as a communication path is connected so as to be able to supply air into or suction air from, the cells.

Furthers each cell, branch includes selector valves connected thereto. The selector valve is formed of a valve element of, for example, a plunger. Each cell branch includes a selector valve (valve element) connected to the pump side and a selector valve (valve element) for releasing the air from the cell branch to the atmosphere. Specifically, cell branch 1 (14a) has a selector valve 60a connected to the pump and a selector valve 62a for releasing itself to atmospheric pressure. Cell branch 2 (14b) has a selector valve 60b connected to the pump and a selector valve 62b for releasing itself to atmospheric pressure. Cell branch 3 (14c) has a selector valve 60c connected to the pump and a selector valve releasing itself to atmospheric pressure.

The selector valve connected to each cell branch may be formed of either, separate selector valves, or a single selector valve. That is, it is possible to provide a single selector valve that can operate to select a state in which the branch is connected to the pump side to be able to inflate and deflate, a state capable of releasing the air to atmospheric pressure, or a state of sealing the cells, in accordance with an opening and closing state of the valve element.

Further, a pressure sensor is connected between the selector valve and the cell branch. A pressure sensor 150a is connected to cell branch 1 (14a), a pressure sensor 150b to cell branch 2 (14b) and a pressure sensor 150c to cell branch 3 (14c). The pressure sensor is able to detect the internal pressure of the cells (branch) connected thereto.

A selector valve 64 is connected to pump unit 50. Therefore, when selector valve 64 is closed and selector valves 60a to 60c are opened, for instance, the same air pressure acts on cell branches 1 to 3.

Figure 3:
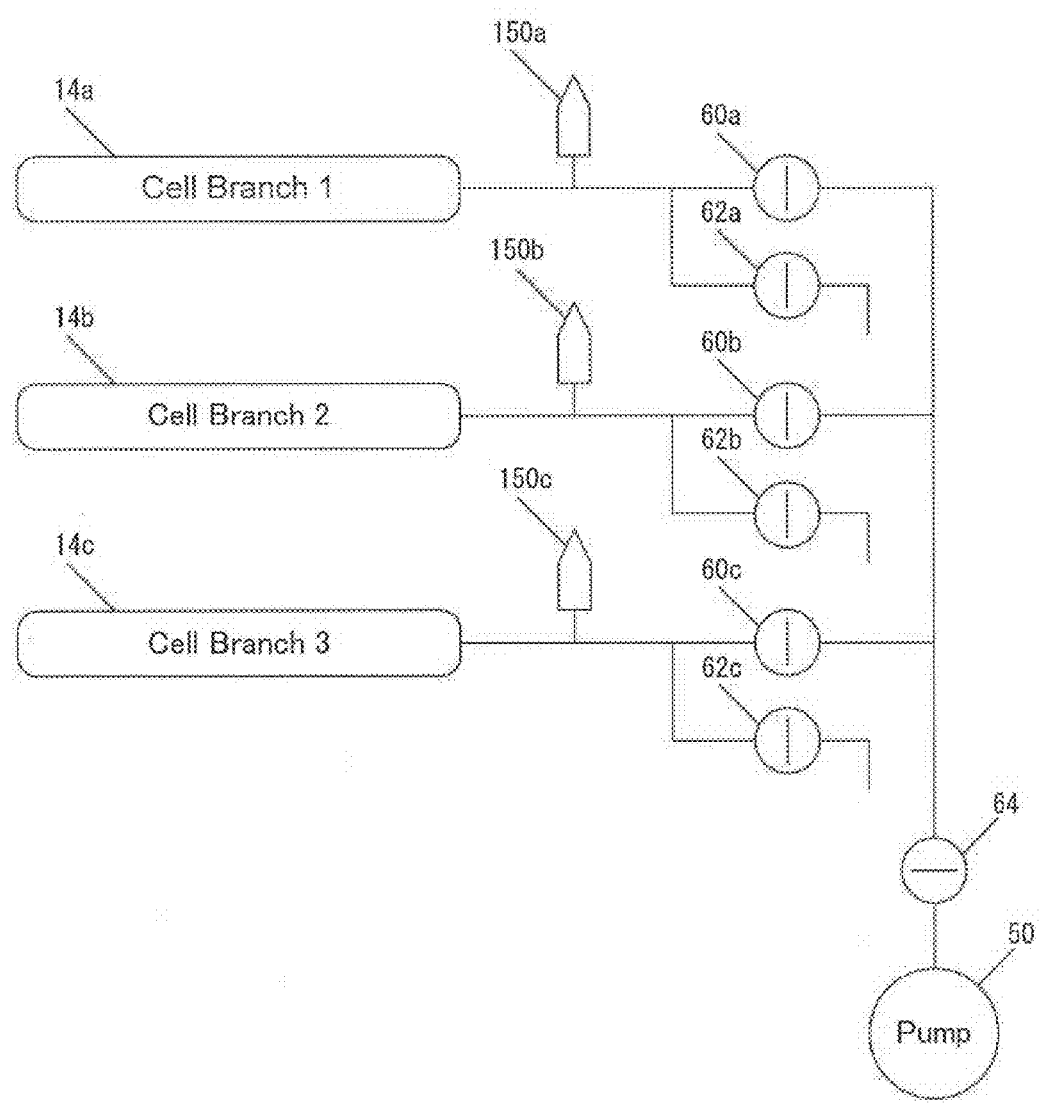
FIG. 3 A diagram for illustrating the operation of selector
valves in the present embodiment.

Now, the operation of the present embodiment will be described using the drawings. To begin with, FIG. 3 shows a state in which all the selector valves are closed. In this state, each of the cell branches has a different pressure from the others.

Figure 4:
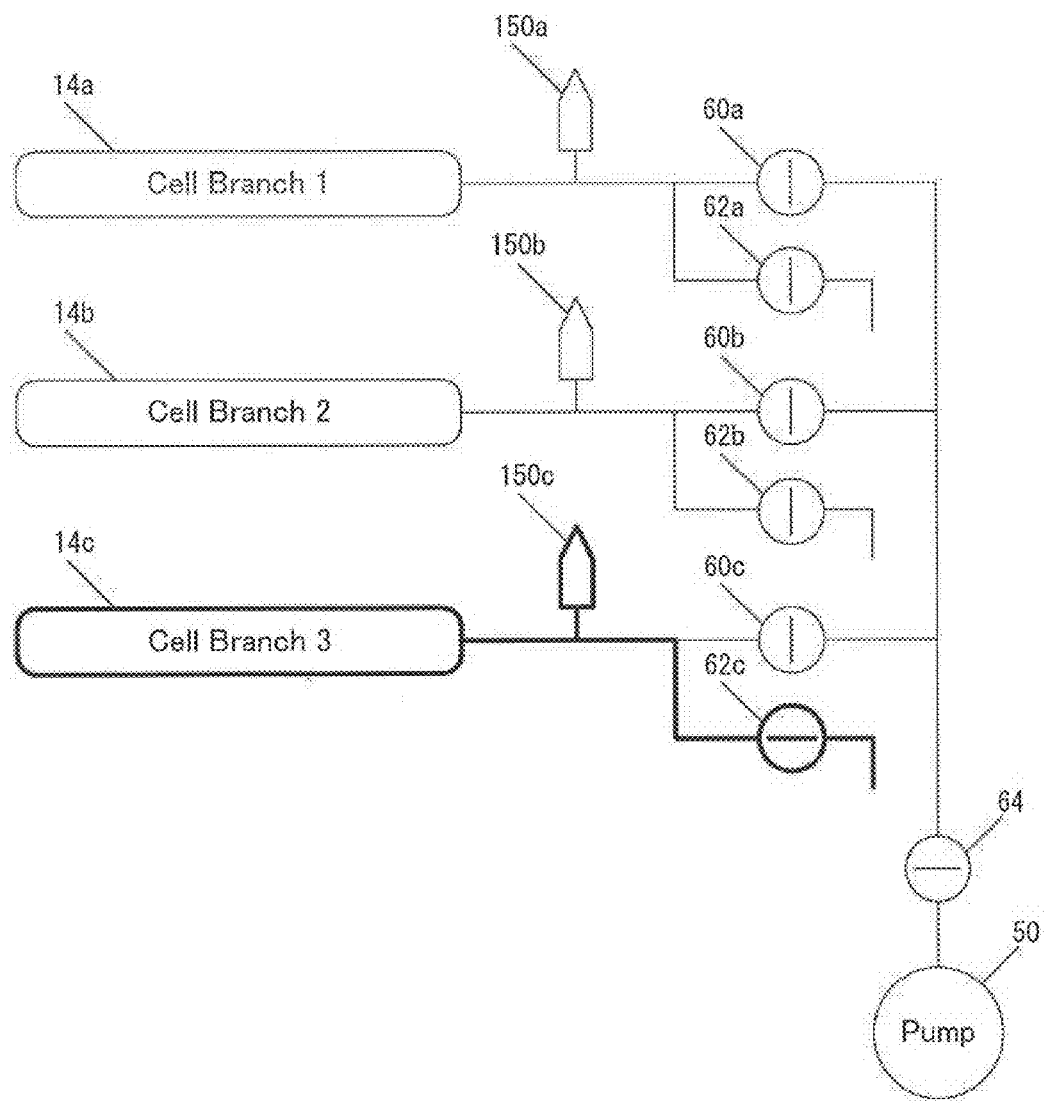
FIG. 4 A diagram for illustrating the operation of selector
values in the present embodiment.

FIG. 4 shows a state in which selector valve 62c of cell branch 3 (14c) is opened. In this state, cell branch 14c is released to atmospheric pressure, so that pressure sensor 150c detects the pressure value of atmospheric pressure.

Figure 5:
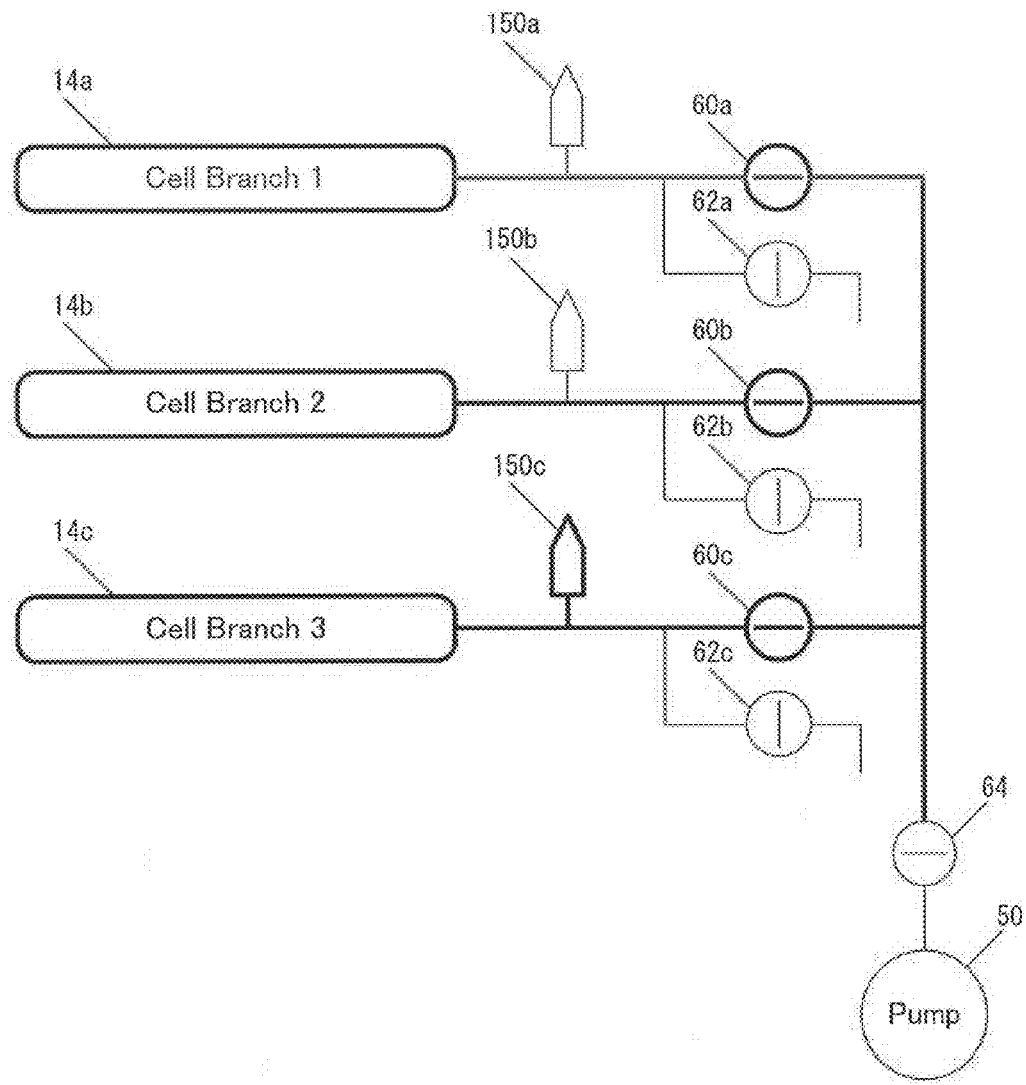
FIG. 5 A diagram for illustrating the operation of selector
values in the present embodiment.

FIG. 5 shows a state in which selector valves 60a to 60c are opened after selector valve 62c has been closed. Since selector valve 64 is also closed, cell branches 1 (14a) to 3 (14c) are communicated so that the same pressure value (internal pressure) is detected.

Figure 6:
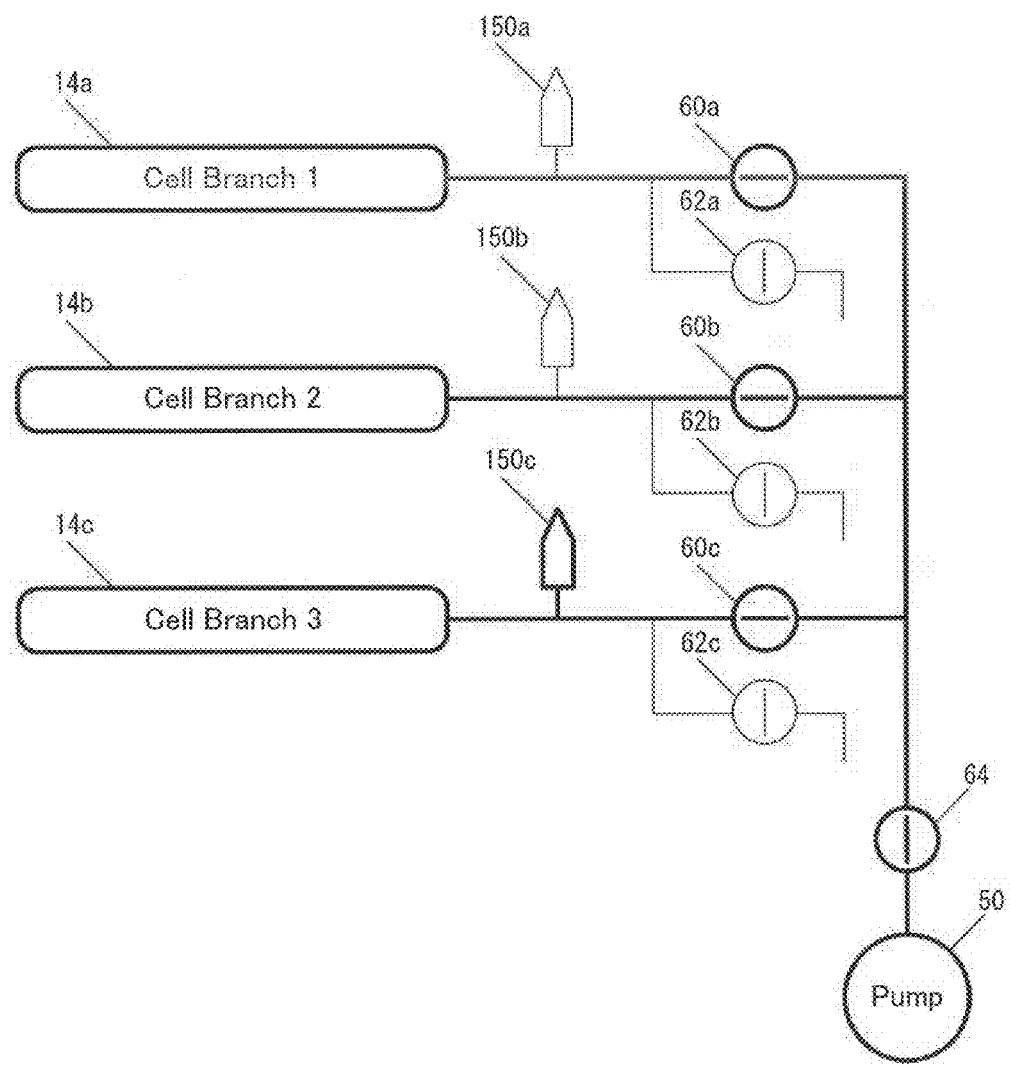
FIG. 6 A diagram for illustrating the operation of selector
valves in the present embodiment.

Subsequently, FIG. 6 shows a state in which selector valve 64 is also opened. In this state, air is supplied to or drawn from the cell branches by the operation of pump unit 50 to thereby adjust the pressure to an appropriate value. In this state, the sensor that detects the pressure value (internal pressure) of the cell branches is pressure sensor 150c that is connected to cell branch 3 (14c).

Figure 7:
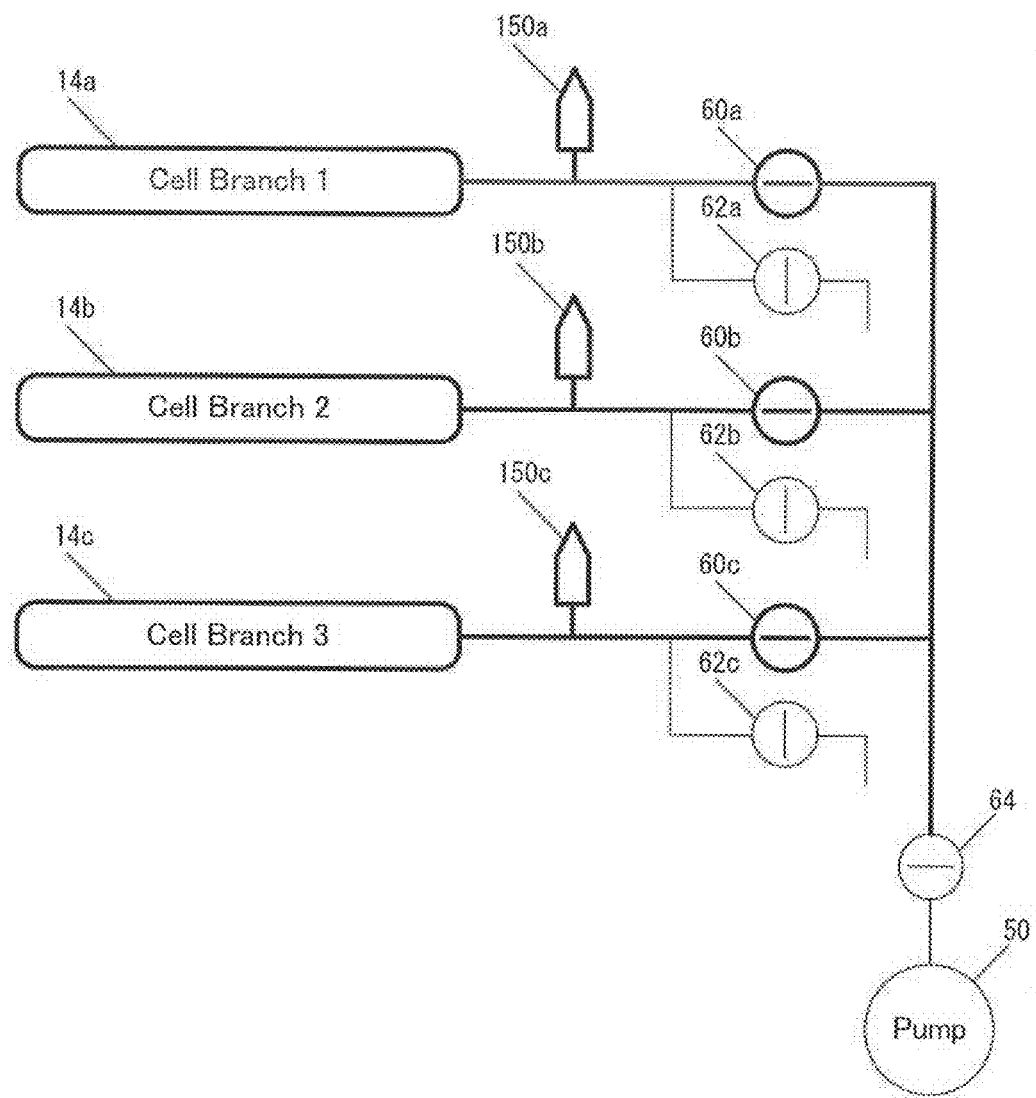
FIG. 7 A diagram for illustrating the operation of selector
values in the present embodiment.

FIG. 7 shows a state in which selector valve 64 is closed. Based on the pressure value (internal pressure) of each cell in this state, zero-point correction can be implemented for each of the pressure sensors.

For description convenience, explanation with FIGS. 3 to 7 has been made in the case of three cell branches. However, by using the above-mentioned method, if there are a plurality of cell branches as in the present embodiment, it is possible to implement zero-point correction all at once for the cells of all the branches, detect the appropriate internal pressure and perform internal pressure adjustment.

2. Functional Configuration

Figure 8:
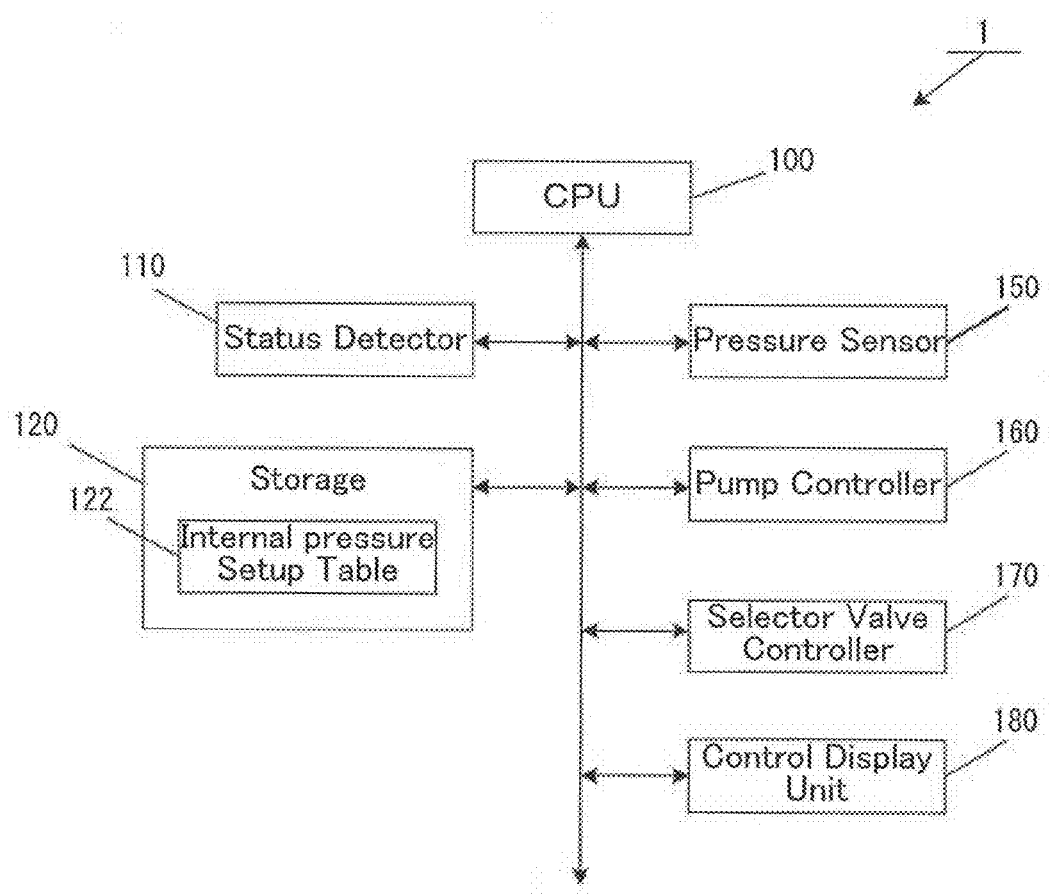
FIG. 8 A diagram for illustrating the functional configuration in the present embodiment.

Next, the functional configuration of bed device 1 will be described using FIG. 3. In bed device 1, CPU 100 is connected to a status detector 110, a storage 120, pressure sensor 150 and a pump controller 160, as shown in FIG. 8.

CPU (Central Process Unit) 100 is a functional unit for controlling bed device 1 as a whole. CPU 100 implements diverse functions by reading and executing various programs stored in storage 120.

Status detector 110 is a functional unit for detecting various states in bed device 1. For example, the detector detects the state by detecting the states of the pressure sensors and detecting the operational signals of the actuators. Herein, as the states to be detected, various states can be detected such as, for example, the back rise angle of the bed, the leg lowering angle, the weight of the patient, and the stay-in-bed state of the patient.

Storage 120 is a functional unit that stores various programs, and various data, required to operate bed device 1.

Storage 120 is configured of semiconductor memories, HDD (Hard Disk Drive) and the like, for example.

Storage 120 also stores an internal pressure setup table 122. Internal pressure setup table is a table that stores the specified internal pressure value for each cell (cell 14) in bed device 1.

Now, one data configuration example of internal pressure setup table 122 will be described with reference to FIG. 9. As shown in FIG. 9, the initial values of the internal pressure value of one cells are stored in relation to the back angles and the patient weights. Each internal pressure value is stored for every cell branch and referred to as required.

Pressure sensor 150 is a functional unit for detecting the pressure of each cell, and is configured of a pressure sensor and she like. Pressure sensor 150 is connected to each selector valve (for each cell branch) via an air blow tube joint connector. The pressure of each cell is detected by pressure sensor 150.

Pump controller 160 is a functional unit for controlling pump unit 50. Control on inflation and deflation can be implemented by making pump unit 50 active and inactive.

A selector valve controller 170 is a functional unit for controlling the selector valve connected to each branch of cells and the selector valve connected to pump unit 50. By controlling the selector valves, it is possible to inflate the cells in cooperation with pump unit 50, deflate the cells, and retain the air in each cell.

A control, display unit 180 severs as an input unit for users (e.g., patients, care-receivers, caregivers, etc.) to instruct the operation of bed device 1 and as a functional unit for informing the user of the conditions of bed device 1. This unit can be configured of a liquid crystal screen including a touch panel or hardware keys, for example.

3. Processing Flow

Figure 10:
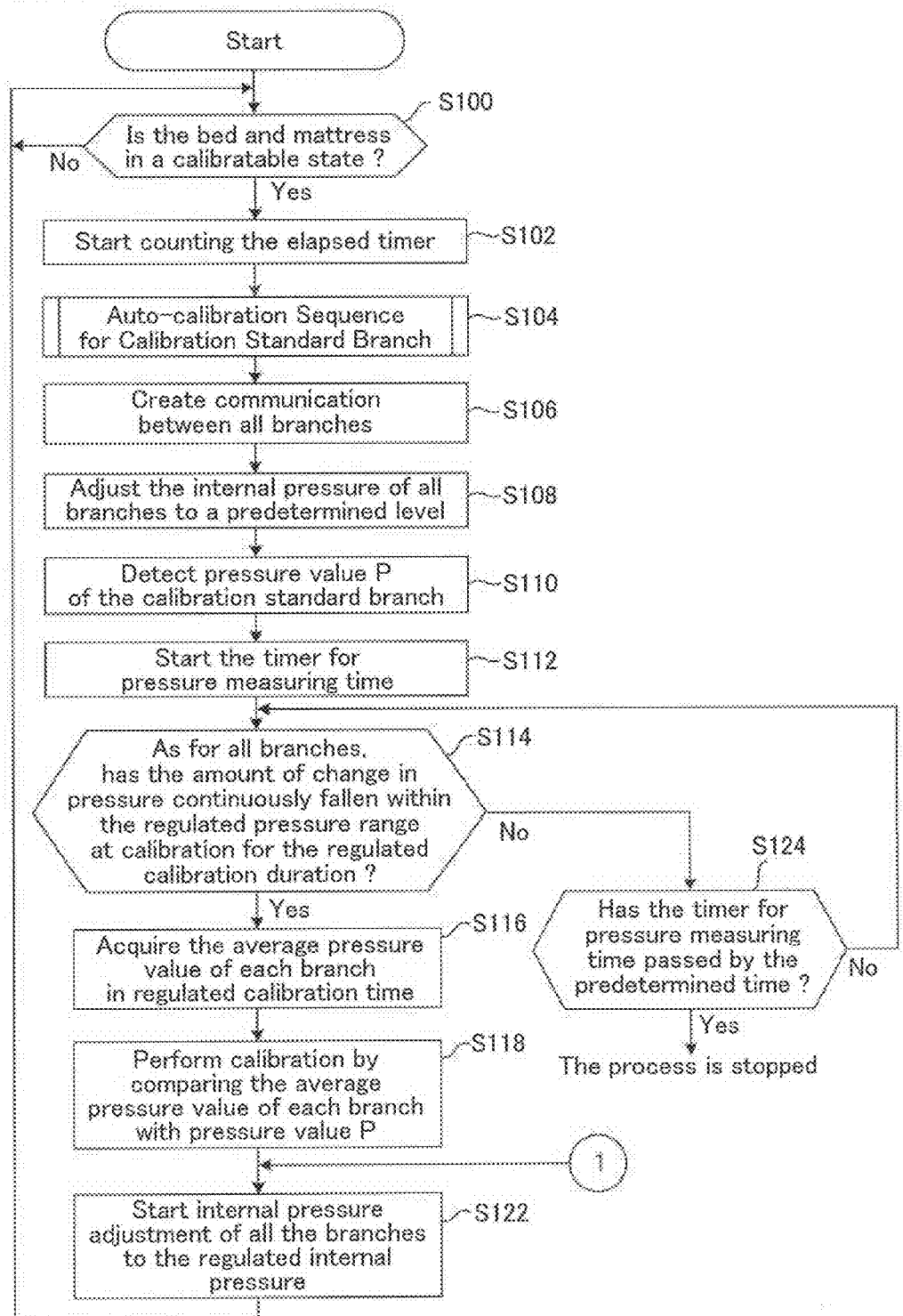
FIG. 10 An operation flow for illustrating the process of the
present embodiment.
Figure 11:
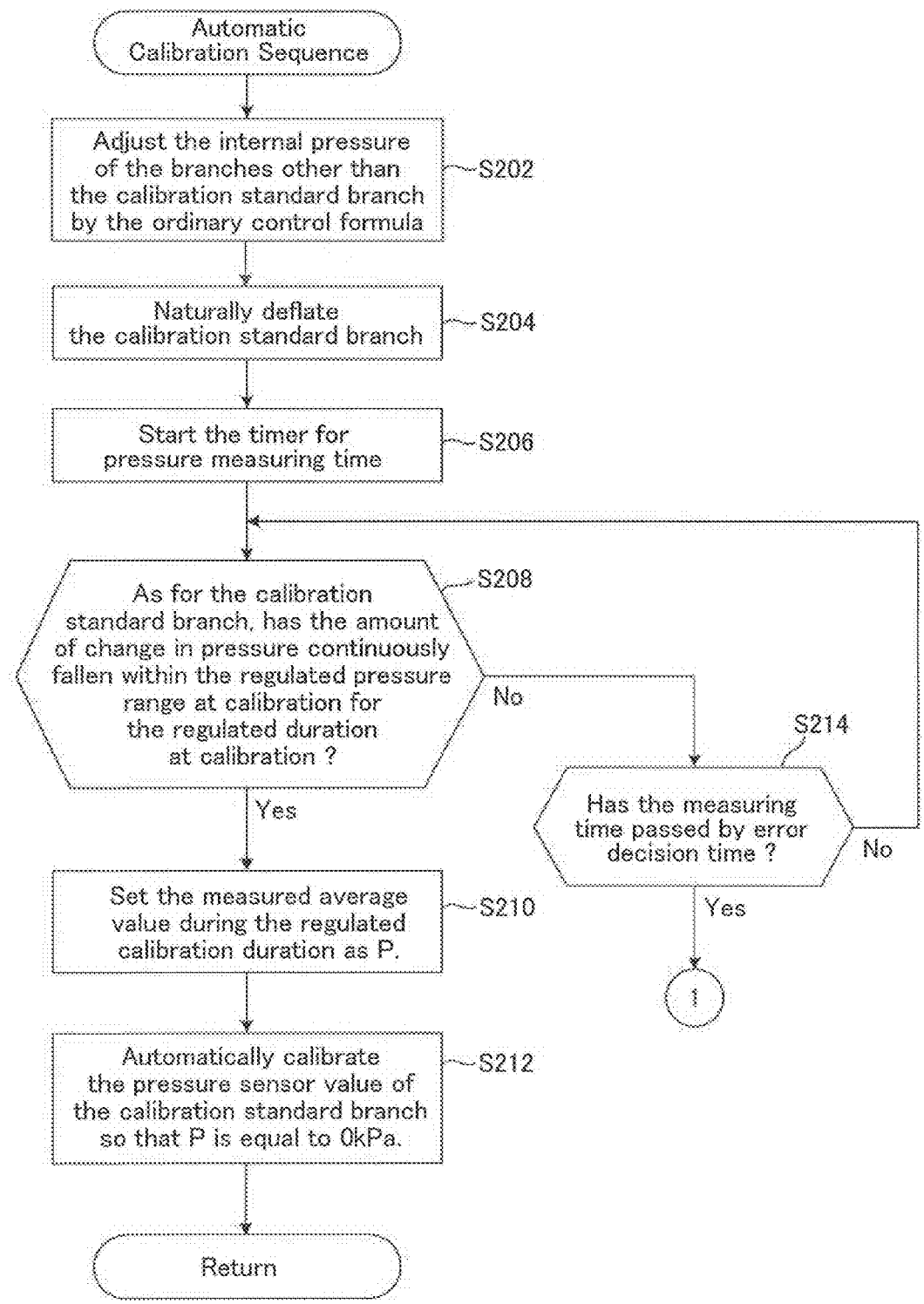
FIG. 11 An operation flow for illustrating the process of the
present embodiment.
Figure 12:
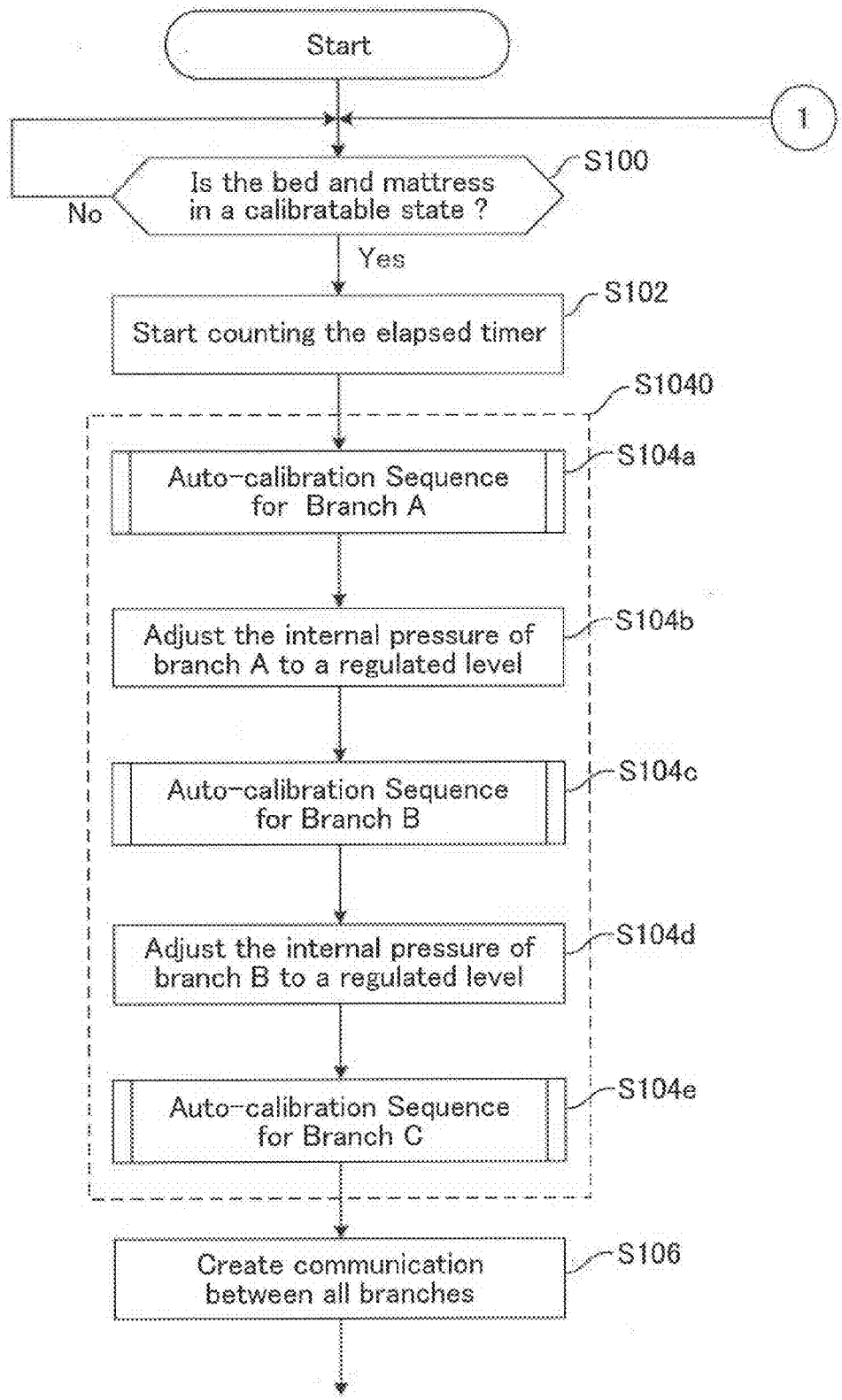
FIG. 12 An operation flow for illustrating a variational
example of the present embodiment.

Next, the processing flow will be described using the drawings. FIGS. 10 to 12 shows a process in the present embodiment relating to zero-point adjustment of pressure sensors that can be performed without releasing the pressure sensors to atmospheric pressure. This process will also be described by taking the case where three cell branches described with FIGS. 3 to 7 are adopted and zero-point adjustment is performed based on cell branch 3.

Herein, as to the timing at which the process of the present embodiment is executed, the operation may be started by explicit instructions of a caregiver or staff, or may be started after a lapse of time (e.g., after a lapse of 12 hours from the previous calibration).

To begin with, it is determined whether the bed is in a calibratable state or whether the mattress is in a calibrated state (Step S100). Here, the calibratable state is determined by checking whether the current state, for example, satisfies the following operating conditions:

the back angle of the bed is less than 4 degrees;
 the knee angle is less than 1 degrees;
 the leg angle is less than 4 degrees;
 the tilt angle of the bed device is 4 degrees or smaller;
 the leg shrinkage is 2 cm or smaller; and,
 the operation mode is in the normal mode.

Then, when the above operational conditions are satisfied (Step S100; Yes), the elapsed timer starts counting (Step S102). In this way, it is possible to perform safe calibration by monitoring the conditions of the bed and the conditions of the mattress and implementing the subject process when the bed is in the calibration state.

Next, automatic calibration for the branch to be the standard for performing the zero-point correction (which will be referred to hereinbelow as "calibration standard branch") is implemented (Step S104). Here, the process shown in FIG. 11 is implemented for the automatic calibration sequence. Now, the automatic calibration sequence will be described with reference to FIG. 11.

First, the other branches than the calibration standard branch are adjusted as to internal pressure based on the ordinary control formula (Step S202). For example, when the automation calibration sequence for cell branch 3 is implemented, internal pressure adjustment on the cell branches 1 and 2 other than cell branch 3, is implemented based on the ordinary control formula.

Here, when internal pressure adjustment is implemented based on the ordinary control formula, internal pressure adjustment is performed based on the internal pressure setup values stored in internal pressure setup table 122.

Subsequently, the calibration standard branch is naturally deflated (Step S204). Thereafter, a timer for pressure measuring time is started (Step S206).

Subsequently, it is determined whether the amount of change of the pressure in the calibration standard branch has continuously fallen within a predetermined regulated pressure range at calibration (within a specified pressure range at calibration) for a predetermined duration at calibration (regulated calibration duration) (Step S208). For example, it is determined whether the amount of change has continuously fallen within ±0.4 kPa as the regulated pressure range at calibration for 5 seconds as the regulated duration at calibration.

Herein, if the amount of change of the pressure cannot continuously fall within the regulated pressure range at calibration for the regulated duration at calibration (Step S208; No), it is then determined whether the measurement time has passed by error decision time (e.g., 1 minute) (Step S214).

When the measurement time has passed by the error decision time (Step S214; Yes), the process goes to Step S122 in FIG. 10.

On the other hand, in the calibration standard branch when the amount of change of the pressure has continuously fallen within the regulated pressure range at calibration for the regulated duration at calibration (Step S208; Yes), then the measured average pressure value during the regulated calibration duration is set as P (Step S210). As an example, the pressure values being measured have been detected for the last five seconds, so that the average of the pressure values being detected is computed, which may be set as P.

Subsequently, the pressure value detected by the pressure sensor of the calibration standard branch is automatically calibrated so that P is equal to 0 kpa (Step S212). As a result, zero-point correction for the pressure sensor for the calibration standard branch can be done based on atmospheric pressure.

Returning to FIG. 10, the process from Step S106 will be described. At this stage, all the branches are made to communicate (Step S106). For example, the selector valves for inflation and deflation are opened. As a resale, all the cell branches (cell branches 1 to 3) have the same internal pressure.

Next, the internal pressures of all the branches are adjusted to predetermined levels (Step S103). Since all the selector valves for inflation and deflation have been released at Step S106, the internal pressures are adjusted to the same pressure value.

After completion of internal pressure adjustment, the pressure sensor connected to the calibration standard branch is used to detect pressure value P (Step S110). Then, the timer for pressure measuring time is started (Stop S112).

Next, it is determined for all the branches, whether the amount of change in pressure has continuously fallen within the regulated pressure range at calibration for the regulated calibration duration (Step S114). Herein, when the amount of change in pressure has not continuously fallen within the regulated range at calibration for the regulated calibration duration or when the amount of change in pressure falls out of the regulated pressure range at calibration (Step S114; No), it is determined whether the timer for pressure measuring time has passed by the predetermined time (Step S124).

When the timer for pressure measuring time has not passed by the predetermined time (Step S124; No), the control returns to Step S114 so as to repeat the process. On the other hand, when the timer for pressure measuring time has passed by the predetermined time (Step S124; Yes), it is decided that an error has occurred, and the process is stopped.

At Step S114, in all the branches, when the amount of change in pressure has continuously fallen within the regulated range during the regulated calibration duration (Step S114; Yes), the average pressure valve of each branch in regulated calibration duration is acquired (Step S116).

Then, the pressure sensor connected to each branch is calibrated by comparing the average pressure value of each branch with pressure value P (Step S118).

After each pressure sensor has been calibrated, internal pressure adjustment is started so that all the branches may have the regulated internal pressure (Step S122).

In this ways according to the process of the present embodiment, it is possible to celebrate all the pressure sensors for all cells of the bed device (air mattress), using only a single cell branch. Upon this, the cell branches are calibrated one to another, so that it is possible to calibrate the pressure sensors no matter the patient is lying or not on the bed device (air mattress).

That is, when the conditions of the mattress or the conditions of the bed device are determined to be in a state in which the pressure sensors can be calibrated, it is possible to calibrate the pressure sensors without regard to whether the patient is staying in the bed, thus bringing about unprecedented significant advantages.

4. Variational Examples

As the embodiment of this invention has been detailed with reference to the drawings, the specific configuration should not be limited to this embodiment, designs and others that do not depart from one gist or this invention should also be included in the scope of claims.

The specific values of the predetermined pressure values, ranges, time and others are given for description purposes in order to promote understanding of the present invention. Therefore, those values should not be interpreted as limitation.

Though the above embodiment has been described by illustrating a case where a single calibration standard branch is used, it is of course possible to use a plurality of calibration standard branches. For example, since, in the case shown in FIG. 2, there are a plurality of branches, more accurate zero-point correction can be done when a plurality of calibration standard branches are used.

For this case, a process shown in FIG. 12, for example is implemented. FIG. 12 is a chart showing only the section corresponding to Steps S100 to S106 in FIG. 10. The process after Step S108 is implemented the same as in FIG. 10. Further, the steps of implementing the same processing are allotted with the same reference numerals. That is, FIG. 12 is a chart in which Step S104 in FIG. 10 is replaced by Step S1040.

In this case, the automatic calibration sequence of FIG. 11 is implemented by handling branch A as the calibration standard branch (Step S104a). After completion of the automatic calibration sequence, the internal pressure of branch A is adjusted to the regulated internal pressure (Step S104b).

Subsequently, the automatic calibration sequence of FIG. 11 is implemented by handling branch B as the calibration standard branch (Step S104c). After completion of the automatic calibration sequence, the internal pressure of branch E is adjusted to the regulated internal pressure (Step S104d).

Then, the automatic calibration sequence of FIG. 11 is implemented by handling branch C as the calibration standard branch (Step S104e). Thus, by using three branches as the calibration standard branch it is possible to perform zero-point correction more accurately.

Further, the above-described embodiment has been described by giving an example in which a cell is divided into the plurality of sections (an example where the cells located near the middle are divided into upper and lower sections). However, each cell may be simply formed as a single cell.

Figure 13:
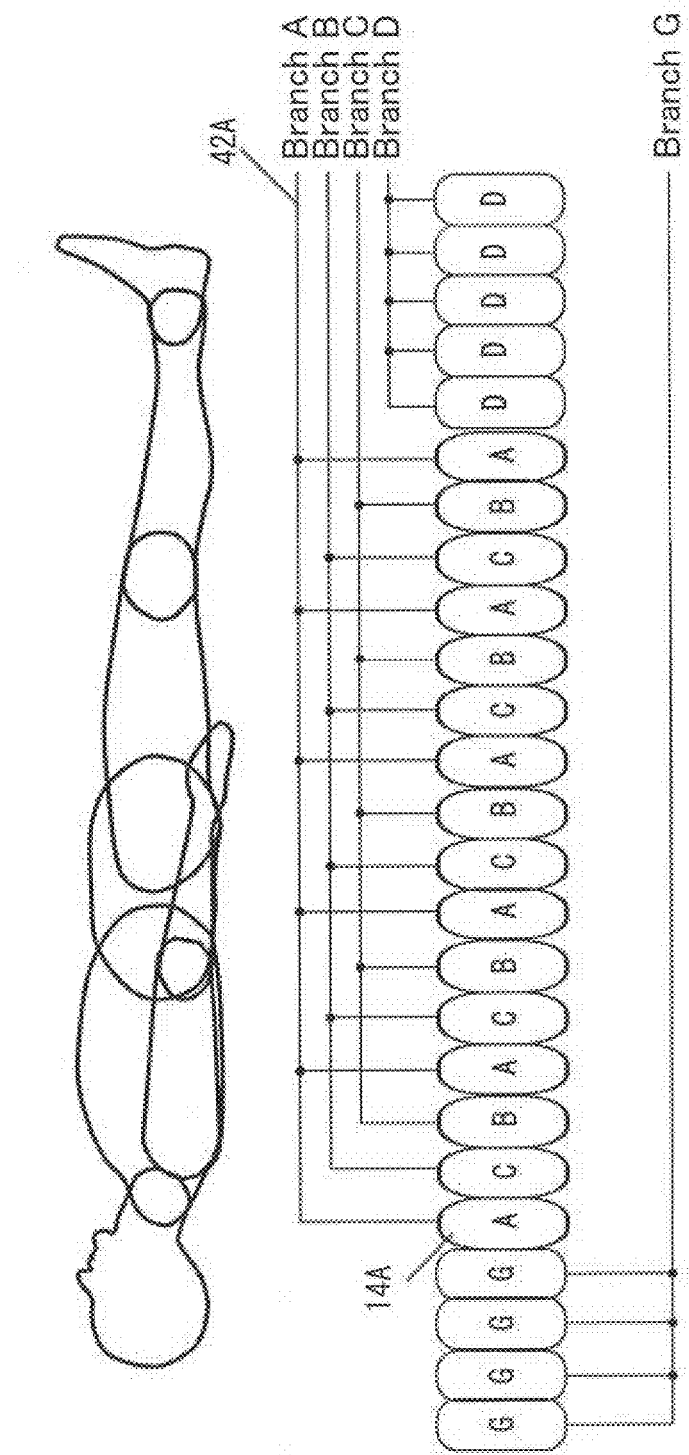
FIG. 13 An operation flow for illustrating a variational
example of the present embodiment.

For example, as shown in FIG. 13, the cells may be simply arranged in the longitudinal direction without being divided, into upper and lower sections, to form the entire air mattress.

Figure 14:
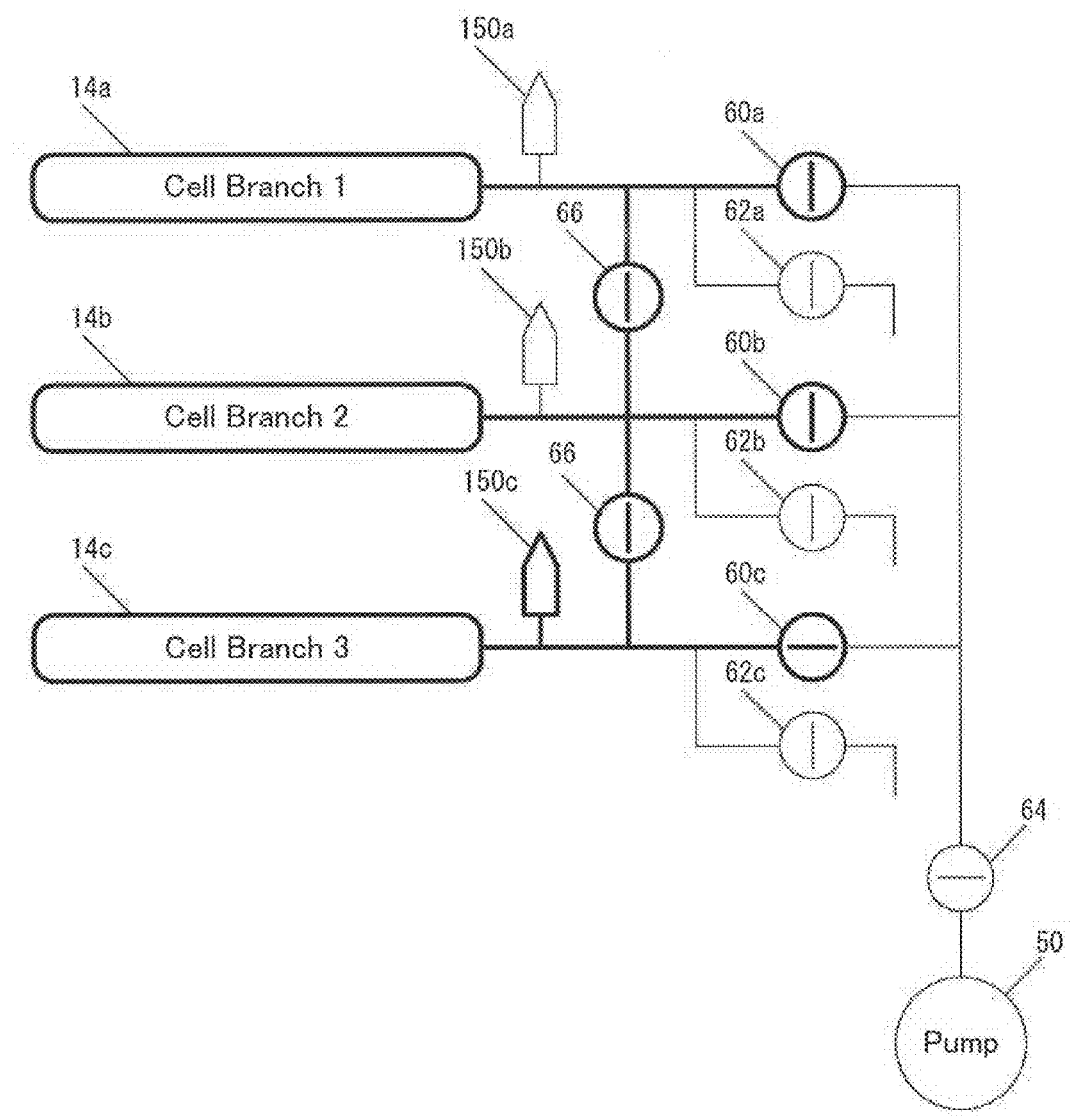
FIG. 14 An operation, flow for illustrating a variational
example of the present embodiment.

Moreover, in the above-described embodiment, all the cells are connected to the pump side to establish communication by opening the selector valves for inflation and deflation at step S106. However, as long as communication between the cells is created, other methods can be used. For example, as shown in FIG. 14, separate selector valves 66 may be arranged between cells, and communication between the cells may be created by opening these selector valves 66.

In the present embodiment, the process for calculating "the average value" may be carried out not only by computing the simple average of the obtained values, but also using other computing methods. For example, the average may be calculated using the data with the maximum and minimum values omitted, or be calculated by using the data with the median further omitted. Alternatively, instead of the simple arithmetic mean, the average may also be calculated by using geometric mean or weighted mean.

DESCRIPTION OF REFERENCE NUMERALS 1 bed device
10 mattress body
12 cover
14 cell
14a, 14b, 14c cell branch
30 base
10 controller
42, 44 air blow tube
50 pump unit
52 control cable
54 control cable
56 power cable
60a, 60b, 60c, 62a, 62b. 62c, 64, 66 selector valve
100 CPU
110 status detector
120 storage
122 internal pressure setup table
150a, 150b, 150c pressure sensor
160 pump controller
170 selector calve controller
180 control display unit

The invention claimed is:

1. A mattress comprising:
   a plurality of cells;
   pressure sensors for detecting the internal pressure of the cells;
   a pump connected to adjust the amount of air in each cell;
   communication paths from the pump to the plurality of cells;
   selector valves, arranged on the communication paths between each of the cells and the pump, and capable of switching between, at least, a state for creating communication between the cell and the pump and a state for opening the cell to atmospheric pressure; and,
   a calibration portion for calibrating the pressure sensors, the calibration portion comprising:
      a calibration determining portion that adopts one cell as a calibration standard cell, determines whether a pressure detected by a pressure sensor connected to the calibration standard cell has continuously fallen within a regulated pressure range at calibration for a regulated duration at calibration when a selector valve connected to the calibration standard cell is opened to atmospheric pressure;
      a first calibration portion that, when the pressure detected by the pressure sensor connected to the calibration standard cell has continuously fallen within the regulated pressure range at calibration for the regulated duration at calibration, performs zero-point adjustment of the pressure sensor connected to the calibration standard cell, based on a pressure value detected by the pressure sensor;
      an internal pressure adjustment portion that creates communication between the plurality of cells to perform internal pressure adjustment of the plurality of cells to a predetermined internal pressure value, based on the pressure value detected by the pressure sensor connected to the calibration standard cell; and,
      a second calibration portion that calibrates each of the pressure sensors connected to the plurality of cells, based on the internal pressure adjusted by the internal pressure adjustment portion.

2. The mattress according to claim 1, wherein the selector valves installed for the plurality of cells are changed over to communicate with the pump so as to make the plurality of cells have the same pressure.

3. The mattress according to claim 2, further comprising a mattress status detecting portion for detecting a state of the mattress,
   wherein the calibration portion performs calibration of the pressure sensors when the mattress is in a state in which calibration of the pressure sensor is calibratable.

4. The mattress according to claim 1, further comprising a mattress status detecting portion for detecting a state of the mattress,
   wherein the calibration portion performs calibration of the pressure sensors when the mattress is in a state in which calibration of the pressure sensor is calibratable.

5. The mattress according to claim 1, further comprising an inter-cell selector valve for creating communication between the plurality of cells,
   wherein the internal pressure adjustment portion opens the inter-cell selector valves to thereby make the plurality of cells have the DOU pressure.

6. The mattress according to claim 5, further comprising a mattress status detecting portion for detecting a state of the mattress,
   wherein the calibration portion performs calibration of the pressure sensors when the mattress is in a state in which calibration of the pressure sensor is calibratable.

7. A pressure sensor calibration method used for a mattress, the mattress comprising:
   a plurality of cells;
   pressure sensors for detecting internal pressure of the cells;
   a pump connected to adjust the amount of air in each cell;
   communication paths from the pump to the plurality of cells; and
   selector valves, arranged on the communication paths between each of the cells and the pump, and capable of switching between, at least, a state for creating communication between the cell and the pump and a state for opening the cell to atmospheric pressure;
a calibration step for calibrating the pressure sensors, comprising the steps of:
   determining whether a pressure detected by a pressure sensor connected to the calibration standard cell has continuously fallen within a regulated pressure range at calibration for a regulated duration at calibration when a selector valve connected to the calibration standard cell is opened to atmospheric pressure;
   performing zero-point adjustment of the pressure sensor connected to the calibration standard cell, based on a pressure value detected by the pressure sensor when the pressure detected by the pressure sensor connected to the calibration standard cell has continuously fallen within the regulated pressure range at calibration for the regulated duration at calibration;
   creating communication between the plurality of cells to perform internal pressure adjustment of the plurality of cells to a predetermined internal pressure value, based on the pressure value detected by the pressure sensor connected to the calibration standard cell; and,
   calibrating each of pressure sensors connected to the plurality of cells, based on the internal pressure adjusted by the internal pressure adjustment means.

8. A bed device comprising:
   a mattress comprising;
      a plurality of cells;
      pressure sensors for detecting internal pressure of the cells;
      a pump connected to adjust the amount of air in each cell; and
      communication paths from the pump to the plurality of cells,
   a bed body;
   selector valves, arranged on the communication paths between each of the cells and the pump, and capable of switching between, at least, a state for creating communication between the cell and the pump and a state for opening the cell to atmospheric pressure; and,
   a calibration portion for calibrating the pressure sensor,
   the calibration portion comprising:
      a calibration determining portion that adopts one cell as a calibration standard cell, determines whether a pressure detected by a pressure sensor connected to the calibration standard cell has continuously fallen within a regulated pressure range at calibration for a regulated duration at calibration when a selector valve connected to the calibration standard cell is opened to atmospheric pressure;
      a first calibration portion that, when the pressure detected by the pressure sensor connected to the calibration standard cell has continuously fallen within the regulated pressure range at calibration for the regulated duration at calibration, performs zero-adjustment of the pressure sensor connected to the calibration standard cell, based on a pressure value detected by the pressure sensor;

an internal pressure adjustment portion that creates communication between the plurality of cells to perform internal pressure adjustment of the plurality of cells to a predetermined internal pressure value, based on the pressure value detected by the pressure sensor connected to the calibration standard cell; and, a second calibration portion that calibrates each of the pressure sensors connected to the plurality of cells, based on the internal pressure adjusted by the internal pressure adjustment portion.

9. The bed device according to claim 8, further comprising a bed status detecting portion for detecting a state of the bed body, wherein the calibration portion performs calibration of the pressure sensors when the bed body is in a state in which calibration of the pressure sensor is calibratable.

* * * * *